US012232771B2

(12) United States Patent
Cabrera et al.

(10) Patent No.: US 12,232,771 B2
(45) Date of Patent: Feb. 25, 2025

(54) MECHANICAL COMPRESSION HERMETIC FORCE SENSORS FOR SURGICAL DEVICES

(71) Applicant: Covidien LP, Mansfield, MA (US)

(72) Inventors: Ramiro D. Cabrera, Cheshire, CT (US); Patrick D. Mozdzierz, Glastonbury, CT (US); Anthony Sgroi, Jr., Southbury, CT (US)

(73) Assignee: Covidien LP, Mansfield, MA (US)

( * ) Notice: Subject to any disclaimer, the term of this patent is extended or adjusted under 35 U.S.C. 154(b) by 502 days.

(21) Appl. No.: 17/716,015

(22) Filed: Apr. 8, 2022

(65) Prior Publication Data

US 2022/0395294 A1 Dec. 15, 2022

Related U.S. Application Data

(60) Provisional application No. 63/209,194, filed on Jun. 10, 2021.

(51) Int. Cl.
*G01L 1/22* (2006.01)
*A61B 17/34* (2006.01)
*A61B 17/00* (2006.01)

(52) U.S. Cl.
CPC ........ *A61B 17/3476* (2013.01); *G01L 1/2287* (2013.01); *A61B 2017/00022* (2013.01); *A61B 2017/00473* (2013.01)

(58) Field of Classification Search
CPC .......................... A61B 17/3476; G01L 1/2287
See application file for complete search history.

(56) References Cited

U.S. PATENT DOCUMENTS

| | | | |
|---|---|---|---|
| 4,420,652 A | 12/1983 | Ikeno | |
| 4,672,418 A | 6/1987 | Moran et al. | |
| 5,041,943 A | 8/1991 | Ilardi et al. | |
| 5,223,741 A | 6/1993 | Bechtel et al. | |
| 5,280,413 A | 1/1994 | Pai | |
| 5,497,290 A | 3/1996 | Fukui et al. | |
| 5,940,279 A | 8/1999 | Gademann et al. | |
| 6,320,128 B1 | 11/2001 | Glovatsky et al. | |
| 6,351,194 B2 | 2/2002 | Takahashi et al. | |
| 6,449,168 B1 | 9/2002 | Soderholm | |
| 7,898,074 B2 | 3/2011 | Eckhardt et al. | |
| 8,354,587 B2 | 1/2013 | Tappel et al. | |
| 8,666,505 B2 | 3/2014 | O'Brien et al. | |
| 8,828,023 B2 | 9/2014 | Neff et al. | |
| 9,442,131 B2 | 9/2016 | Hazel et al. | |
| 10,111,684 B2 | 10/2018 | Williams | |
| 10,327,779 B2 | 6/2019 | Richard et al. | |

(Continued)

OTHER PUBLICATIONS

International Search Report and Written Opinion issued in corresponding International Application No. PCT/IB2022/055303 dated Sep. 16, 2022, 10 pages.

*Primary Examiner* — Eric S. McCall

(57) ABSTRACT

A force sensor includes a substrate, sensing elements, a flex cable, and a seal assembly. The substrate has proximal and distal surfaces, and a cavity defined therein. The sensing elements are disposed within the cavity of the substrate and the pin block assembly is electrically coupled to the sensing elements. The seal assembly includes at least one gasket, a retainer plate, and a seal restraint. The seal assembly is held under compressive load to seal the cavity of the substrate and protect the sensing element disposed therein.

20 Claims, 13 Drawing Sheets

(56) References Cited

U.S. PATENT DOCUMENTS

| | | |
|---|---|---|
| 10,345,165 B2 | 7/2019 | Sgroi, Jr. |
| 10,426,468 B2 | 10/2019 | Contini et al. |
| 10,765,428 B2 | 9/2020 | Sgroi, Jr. |
| 10,959,800 B2 | 3/2021 | Cabrera |
| 2018/0042610 A1 | 2/2018 | Sgroi, Jr. |
| 2018/0067004 A1* | 3/2018 | Sgroi, Jr. ................. G01L 1/26 |

* cited by examiner

MECHANICAL COMPRESSION HERMETIC FORCE SENSORS FOR SURGICAL DEVICES

CROSS-REFERENCE TO RELATED APPLICATIONS

The present application claims the benefit of and priority to U.S. Provisional Patent Application Ser. No. 63/209,194, filed on Jun. 10, 2021, the entire content of which being hereby incorporated by reference.

FIELD

The present application generally relates to surgical devices, and more particularly, to force sensors for powered surgical devices.

BACKGROUND

Force sensors (e.g., load reading sensors) have been used to enhance control of functions in a surgical device, such as a surgical stapling instrument. By using a force sensor, the clamping, stapling, and cutting forces of the surgical device can be monitored and used to facilitate these various functions. The force sensor can be used to detect pre-set loads and cause the surgical device to react in response thereto. For example, during clamping of thick tissue, the load will rise to a pre-determined limit where the surgical device can slow clamping to maintain the clamping force as the tissue relaxes. This allows for clamping of thick tissue without damage to such tissue (e.g., serosa tears). One such example is the firing of a circular stapler type surgical device to create an anastomosis for a powered EEA device (e.g., End-to-End Anastomosis device). The intelligence of such a surgical device is at a higher product cost compared to currently available disposable units and thus would benefit if such intelligent devices are reusable.

Reusable surgical devices must be cleaned (e.g., disinfected) using high pH solutions and sterilized prior to subsequent uses. The most common method of sterilization is the use of autoclaving. Autoclaving utilizes high pressure superheated steam (e.g., 37 PSI @ 137° C. for 18 minutes). Such an environment is known to damage electronic components. For example, surgical devices may suffer from moisture ingress during cleaning and/or sterilizing procedures which, in turn, may corrode and/or degrade the electronic components.

It would be beneficial if the durability of the electronic components of the reusable surgical devices is enhanced to withstand cleaning and sterilization procedures (e.g., the electronic components are protected from high temperatures, steam, and/or moisture), thereby improving the reliability of the electronic components and/or extending the effective cycle life of the surgical device at a cost reduction and with improved manufacturability.

SUMMARY

The force sensors of the present disclosure are sealed to withstand environmental stresses associated with high pH cleaning and sterilization (e.g., autowashing and/or autoclaving), minimizing and/or eliminating the ingress of fluids during such processes thereby rendering the force sensors more durable for re-use.

The force sensors utilize a seal assembly held under mechanical compressive load to protect electronic components of the force sensor. The seal assembly may reduce or eliminate the use of expensive parts and/or intensive processes, such as laser welding, leak testing, and/or molded plastic potting, thereby providing a cost reduction over conventional force sensors. Further, the reduction or elimination of process control needs associated with welding and potting methods improves the design and manufacture of the force sensor and enables disassembly for error correction or salvage of components which improves production yield and reduces scrap. The seal assembly may reduce or eliminate the need for coatings thereby attaining greater reliability cycles.

In one aspect of the present disclosure, a force sensor includes a substrate, sensing elements, a pin block assembly, a first gasket, a flex cable, a second gasket, a retainer plate, and a seal restraint. The substrate has proximal and distal surfaces, and defines a cavity therein that is open to the proximal surface. The sensing elements are disposed within the cavity of the substrate. The pin block assembly is mounted within the cavity of the substrate and electrically coupled to the sensing elements. The first gasket is disposed within the cavity of the substrate over the pin block assembly. The flex cable is positioned against the proximal surface of the substrate over the cavity and is electrically coupled to the pin block assembly. The second gasket is positioned over the flex cable and the retainer plate is positioned over the second gasket. The seal restraint is coupled to the substrate and extends over the retainer plate. The seal restraint applies pressure on the retainer plate and compresses the second gasket against the flex cable to seal the cavity of the substrate.

In aspects, the sensing elements are strain gauges.

In aspects, the pin block assembly includes a block body and pins extending through the block body. Each of the pins has a proximal portion and a distal portion extending proximally and distally, respectively, from the block body. The proximal portions of the pins extend proximally out of the cavity of the substrate and the distal portions of the pins are disposed within the cavity. In some aspects, the first gasket defines at least one opening therethrough, and the proximal portions of the pins of the pin block assembly extend proximally through the at least one opening of the first gasket. In some aspects, the flex cable includes a plurality of apertures defined therethrough, and the proximal portions of the pins of the pin block assembly extend proximally through the plurality of apertures. In some aspects, the second gasket defines openings therethrough, and the proximal portions of the pins of the pin block assembly are disposed within the openings of the second gasket.

In some aspects, the flex cable is wrapped over a proximal end of the second gasket, and the retainer plate is positioned against the flex cable.

In aspects, the cavity of the substrate is open to the distal surface, and the force sensor further includes an electronics assembly electrically coupled to the pin block assembly and extending distally out of the cavity. In some aspects, the force sensor further includes a cover disposed over the electronics assembly and positioned against the distal surface of the substrate over the cavity. The seal restraint extends over and compresses the cover against the distal surface to seal the cavity on the distal surface of the substrate. In certain aspects, the seal restraint is a compression clip including a proximal wall engaged with the retainer plate and a distal wall engaged with the cover.

In another aspect of the present disclosure, a surgical device includes a powered handle assembly, an adapter assembly including a distal connector housing and a trocar connection housing, an end effector releasably secured to the distal connector housing of the adapter assembly, and the force sensor described above disposed between the distal connector housing and the trocar connection housing. The force sensor is configured to measure forces exhibited by the end effector along a load path.

In aspects, the flex cable is electrically coupled to the powered handle assembly and the end effector assembly such that the forces measured by the force sensor is communicated to the powered handle assembly to affect a function of the end effector.

In yet another aspect of the present disclosure, a force sensor includes a substrate, sensing elements, a pin block assembly, a first gasket, a flex cable, a second gasket, a retainer plate, and a seal restraint. The substrate has proximal and distal surfaces, and defines a cavity therein open to the proximal surface. The sensing elements are disposed within the cavity of the substrate. The pin block assembly is mounted on the proximal surface of the substrate over the cavity and is electrically coupled to the sensing elements. The first gasket is positioned over the pin block assembly, the flex cable is positioned over the first gasket and electrically coupled to the pin block assembly, the second gasket is positioned over the flex cable, the retainer plate is positioned over the second gasket, and the seal restraint is coupled to the substrate. The seal restraint applies pressure on the retainer plate and compresses the second gasket, the flex cable, the first gasket, and the pin block assembly against the proximal surface of the substrate to seal the cavity of the substrate.

In aspects, the sensing elements are strain gauges.

In some aspects, the pin block assembly includes a block body and pins extending through the block body. Each of the pins has a proximal portion and a distal portion extending proximally and distally, respectively, from the block body. The distal portions of the pins are disposed within the cavity.

In aspects, the proximal surface of the substrate includes holes defined therein, and the seal restraint extends into the holes. In some aspects, each of the first gasket, the flex cable, the second gasket, and the retainer plate define through holes therethrough that are aligned with the holes defined in the substrate. In certain aspects, the seal restraint is screws extending through the through holes of the retainer plate, the second gasket, the flex cable, and the first gasket, and into the holes of the substrate.

In aspects, the cavity of the substrate is open to the distal surface, and the force sensor further includes an electronics assembly electrically coupled to the pin block assembly and extending distally out of the cavity. In some aspects, the force sensor further includes a cover disposed over the electronics assembly and positioned against the distal surface of the substrate to seal the cavity on the distal surface of the substrate.

The details of one or more aspects of this disclosure are set forth in the accompanying drawings and the description below. Other aspects, as well as features, objects, and advantages of the aspects described in this disclosure will be apparent from the description and drawings, and from the claims.

BRIEF DESCRIPTION OF DRAWINGS

Various aspects of the present disclosure are described hereinbelow with reference to the drawings, which are incorporated in and constitute a part of this specification, wherein.

DETAILED DESCRIPTION

Figure 1:
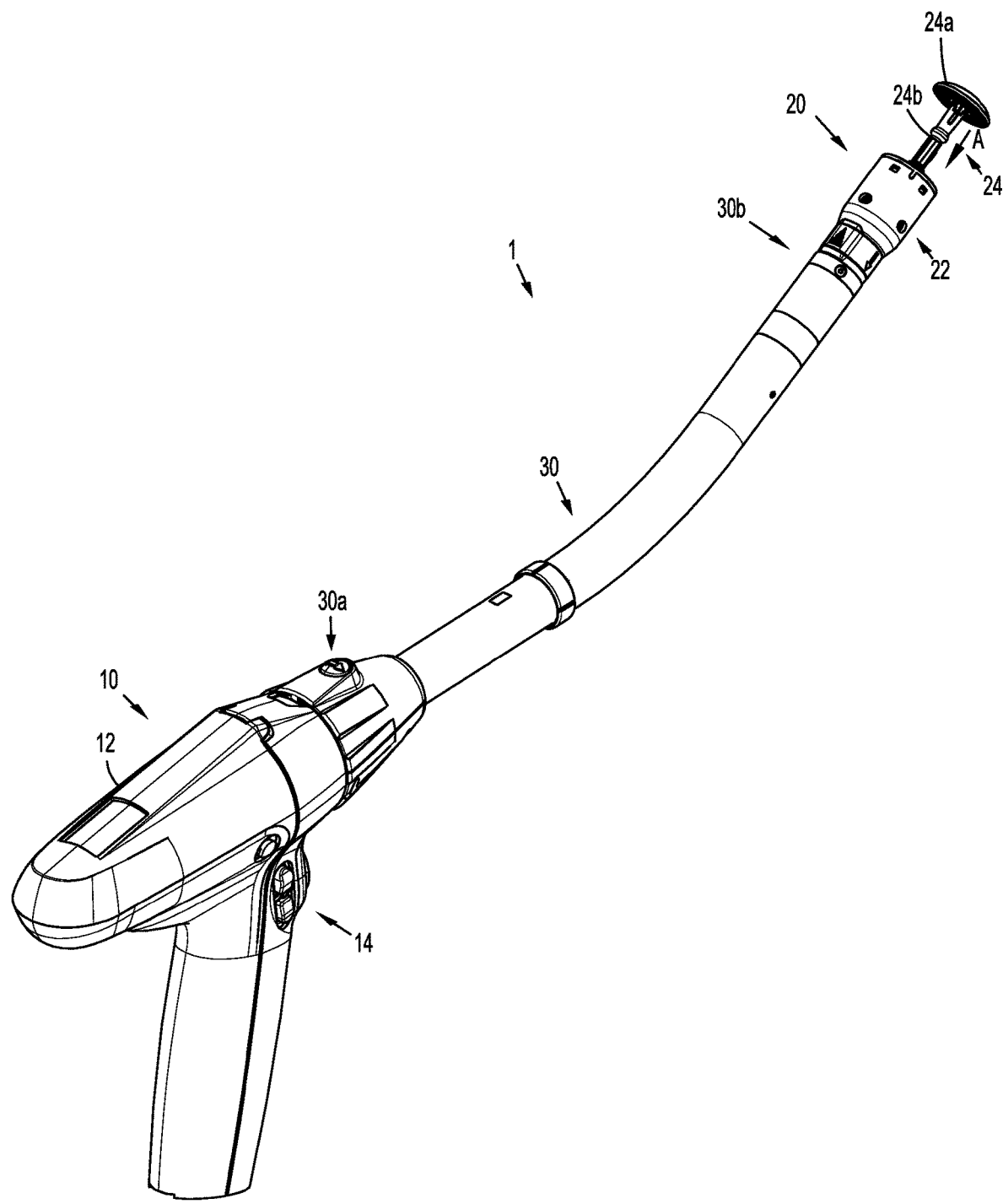
FIG. 1 is a perspective view of a surgical device in accordance with an aspect of the present disclosure.

The force sensors of the present disclosure of, e.g., surgical devices, include electronic components that are protected from harsh environments, such as autowashing and/or autoclaving. The force sensors include a substrate having sensing elements, such as strain gauges and their supporting electronics, mounted therein, which are covered by a seal assembly to create a protective leak-proof barrier to the sensing elements.

Aspects of the present disclosure are now described in detail with reference to the drawings in which like reference numerals designate identical or corresponding elements in each of the several views. Throughout this description, the term "proximal" refers to a portion of a device, or component thereof, that is closer to a hand of a user, and the term "distal" refers to a portion of the device, or component thereof, that is farther from the hand of the user.

Turning now to FIG. 1, a surgical device 1, in accordance with an aspect of the present disclosure, is in the form of a powered handheld electromechanical instrument. The surgical device 1 includes a powered handle assembly 10, a tool assembly or end effector 20, and an adapter assembly 30 interconnecting the powered handle assembly 10 and the end effector 20. The powered handle assembly 10 is configured for selective connection with the adapter assembly 30 and, in turn, the adapter assembly 30 is configured for selective connection with the end effector 20.

The surgical device 1 will further be described to the extent necessary to disclose aspects of the present disclosure. Additionally, while described and shown as including powered handle assembly 10, end effector 20, and adapter assembly 30, it should be understood that a variety of different handle assemblies, end effectors, and/or adapter assemblies may be utilized with aspects of the present disclosure. For a detailed description of the structure and function of exemplary surgical devices, reference may be made to U.S. Pat. Nos. 10,327,779 and 10,426,468, the entire contents of each of which are incorporated herein by reference.

With continued reference to FIG. 1, the powered handle assembly 10 includes a handle housing 12 housing a power-pack (not shown) configured to power and control various operations of the surgical device 1, and a plurality of actuators 14 (e.g., finger-actuated control buttons, knobs, toggles, slides, interfaces, and the like) for activating various functions of the surgical device 1. The end effector 20 includes a loading unit 22 having a plurality of staples (not shown) disposed therein and an anvil assembly 24 including an anvil head 24a and an anvil rod 24b. The adapter assembly 30 includes a proximal portion 30a configured for operable connection to the handle assembly 10 and a distal portion 30b configured for operable connection to the end effector 20.

Figure 2:
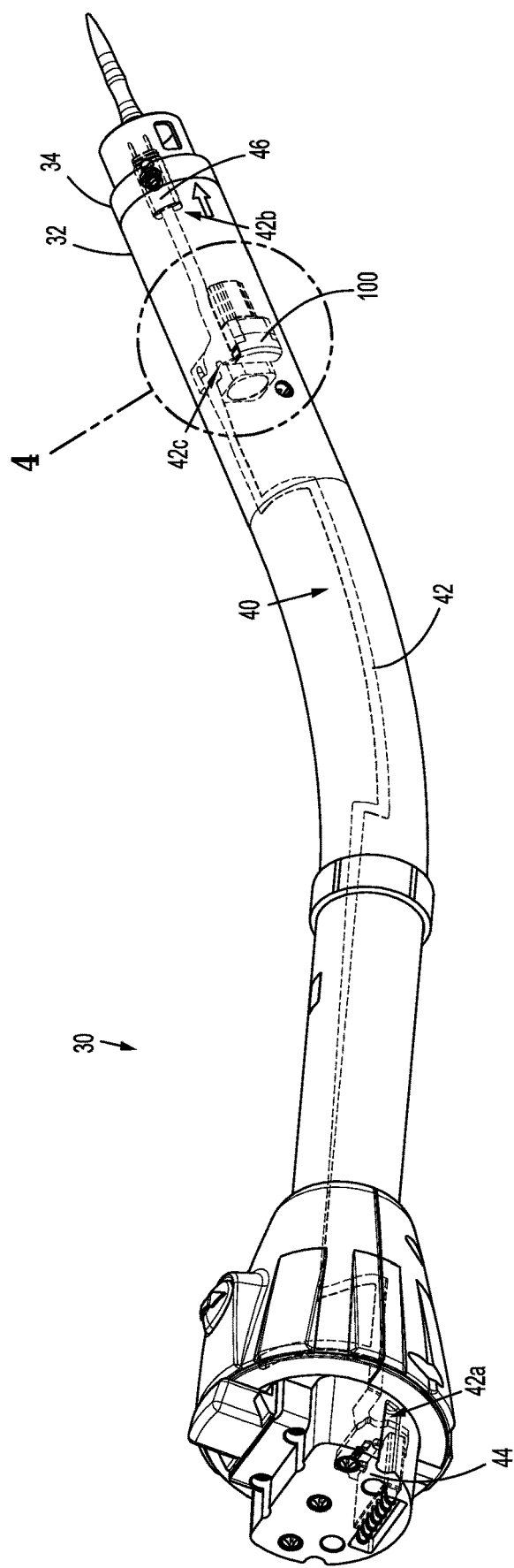
FIG. 2 is a perspective view of an adapter assembly of the surgical device of FIG. 1.

Referring now to FIG. 2, the adapter assembly 30 includes an outer sleeve 32 and a distal connector housing 34 secured to a distal end of the outer sleeve 32. The distal connector housing 34 is configured to releasably secure an end effector, e.g., the end effector 20 (FIG. 1), to the adapter assembly 30. The adapter assembly 30 includes a wiring assembly 40 (shown in phantom) disposed therein. The wiring assembly 40 is configured to enable communication between the handle assembly 10 (FIG. 1) and the end effector 20 (FIG. 1) and to relay power from the handle assembly 10 to the end effector 20. For example, this communication allows for calibration and communication of data and control signals between the end effector 20 and the adapter assembly 30, as well as between the adapter assembly 30 and the handle assembly 10, thereby transferring data pertaining to the end effector 20 to the handle assembly 10 and signals from the handle assembly 10 to the end effector 20. The wiring assembly 40 includes a force sensor 100 that detects stimuli (e.g., strain), converts the stimuli into electrical signals, and sends that data to the handle assembly 10 to affect a function of the end effector 20. It should be understood while described and shown as a force sensor and, more specifically, as a strain gauge, other types of sensors may additionally or alternatively be utilized in the anvil assembly 30.

The wiring assembly 40 generally includes at least one flex cable 42, as well as first and second electrical connectors 44, 46 and the force sensor 100 coupled to the flex cable 42. The flex cable 42 extends the length of the adapter assembly 30 and includes electrical contact regions (not shown) at terminal ends of conductive traces (not shown) defined therethrough for electrical connection with the first and second electrical connectors 44, 46 and the force sensor 100. The flex cable 42 includes a first or proximal end portion 42a coupled to the first electrical connector 44 for electrical connection with the handle assembly 10 (FIG. 1), a second or distal end portion 42b coupled to the second electrical connector 46 for electrical connection with the end effector 20 (FIG. 1), and a third or intermediate end portion 42c electrically coupled to the force sensor 100. In aspects, the flex cable 42 supports electronic components thereon (e.g., surface mount technology and/or through-hole technology, including, for example, integrated circuits (e.g., microchips, microcontrollers, microprocessors), resistors, amplifiers, inductors, capacitors, sensing elements (e.g., optical sensors, pressure sensors, capacitive sensors), buttons, switches, circuit boards, electrical connectors, cables, and/or wires, among other elements or circuitry within the purview of those skilled in the art). It should be understood that the flex cable 42 may be one of a plurality of cables (e.g., flex cables, adapter cables, etc.) electrically coupled together to form a wiring harness, as is within the purview of those skilled in the art.

Figure 3A:
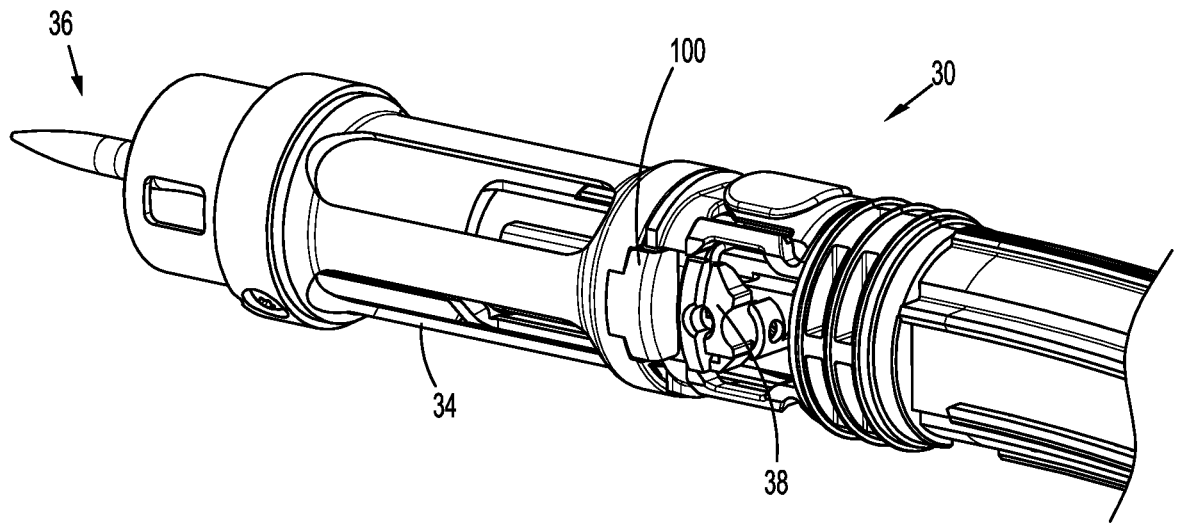
FIG. 3A is a perspective view of a distal end portion of the adapter assembly of FIGS. 1 and 2, with an outer sleeve of the adapter assembly removed therefrom.

As shown in FIG. 3A, the adapter assembly 30 further includes a trocar assembly 36 that extends through a central aperture 101 (see e.g., FIG. 4) of the force sensor 100 and a central aperture 39 (FIG. 3B) of a trocar connection housing 38. The trocar connection housing 38 releasably secures the trocar assembly 36 relative to the outer sleeve 32 (FIG. 2) of the adapter assembly 30. The force sensor 100 is disposed between the trocar connection housing 38 and the distal connector housing 34 of the adapter assembly 30, and is configured to measure forces along a load path. Specifically, the force sensor 100 measures forces of the end effector 20 (e.g., as shown in FIG. 1, the pressure applied by the anvil head 24a in the direction of arrow "A" against the distal portion 30b of the adapter assembly 30, the pressure applied by tissue acting on the anvil head 24a in a direction opposite of arrow "A" as the anvil head 24a is closed onto tissue, etc.).

Figure 3B:
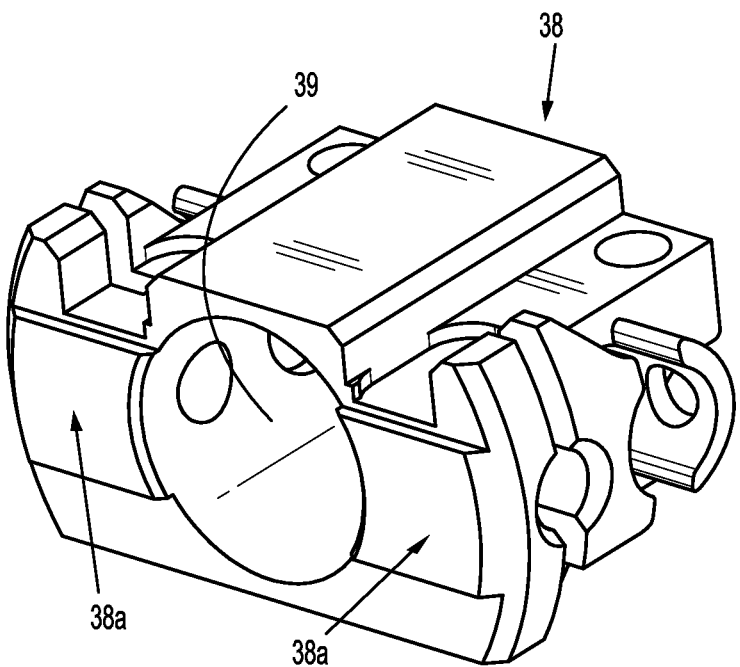
FIG. 3B is an enlarged perspective view of a trocar connection housing of the adapter assembly of FIG. 3A.
Figure 3C:
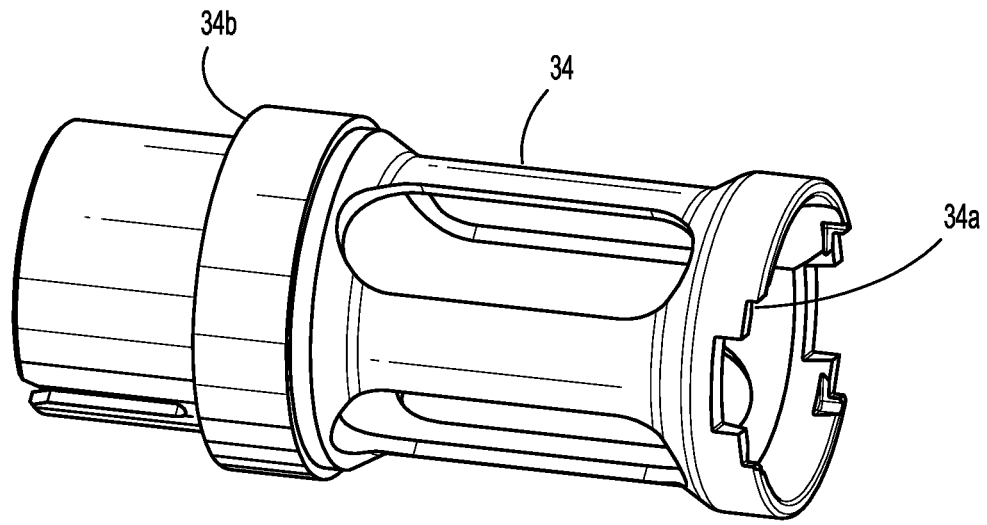
FIG. 3C is an enlarged perspective view of a connector housing of the adapter assembly of FIG. 3A.
Figure 4:
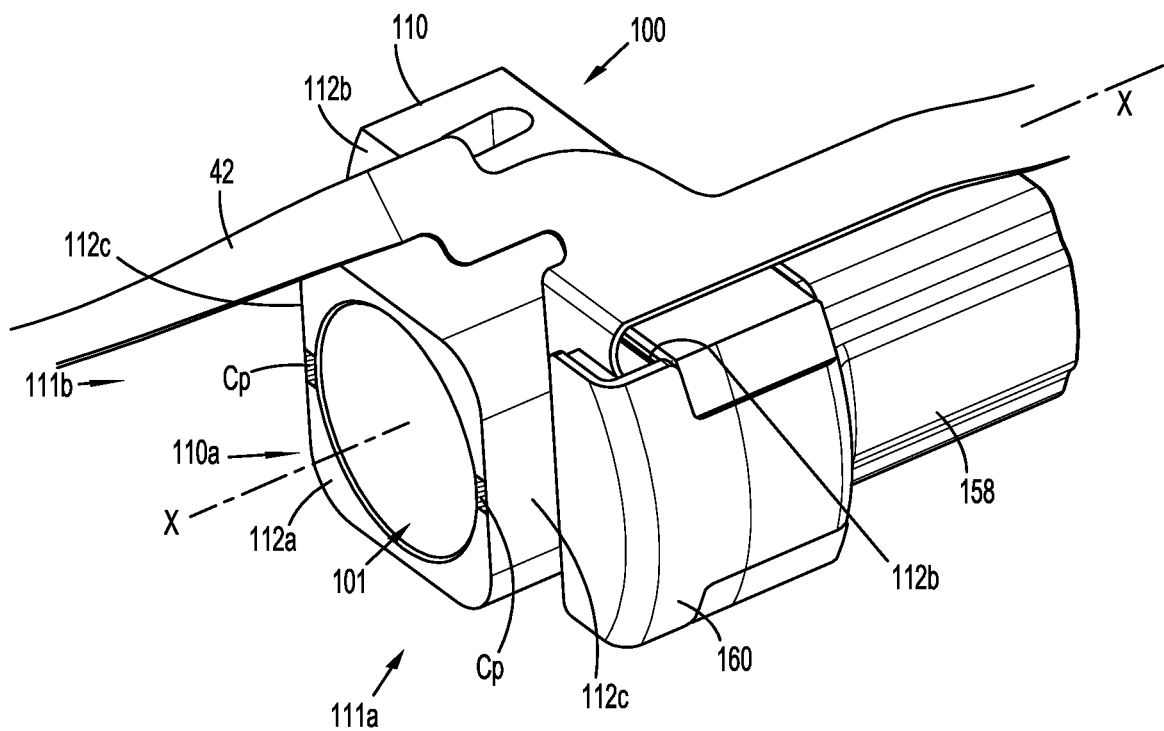
FIGS. 4-6 are perspective views of a force sensor of the surgical device of FIG. 1 in accordance with an aspect of the present disclosure.
Figure 5:
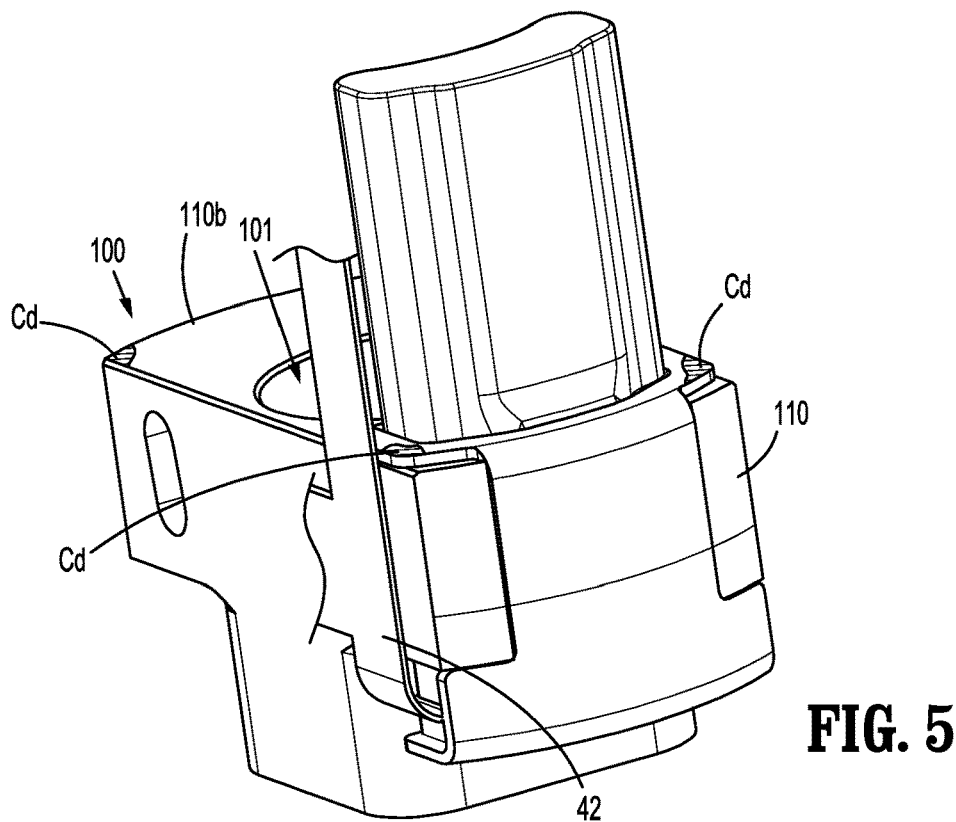

As shown in FIGS. 3B and 4, the trocar connection housing 38 includes a distal surface 38a which interfaces with and loads a proximal surface 110a of a body or substrate 110 of the force sensor 100 at proximal load contact areas "Cp". As shown in FIGS. 3C and 5, a proximal surface 34a of the distal connector housing 34 interfaces with and loads a distal surface 110b of the substrate 110 of the force sensor 100 at distal load contact areas "Cd" (e.g., disposed in each of the corners of the distal surface 110b). Thus, for example, as the anvil assembly 24 (FIG. 1) is approximated towards the loading unit 22 (FIG. 1) of the end effector 20 during clamping and/or stapling of tissue, the anvil head 24a applies uniform pressure in the direction of arrow "A" (FIG. 1) against the distal end 34b of the distal connector housing 34 which, in turn, is transmitted to the distal load contact areas "Cd" of the force sensor 100.

Figure 6:
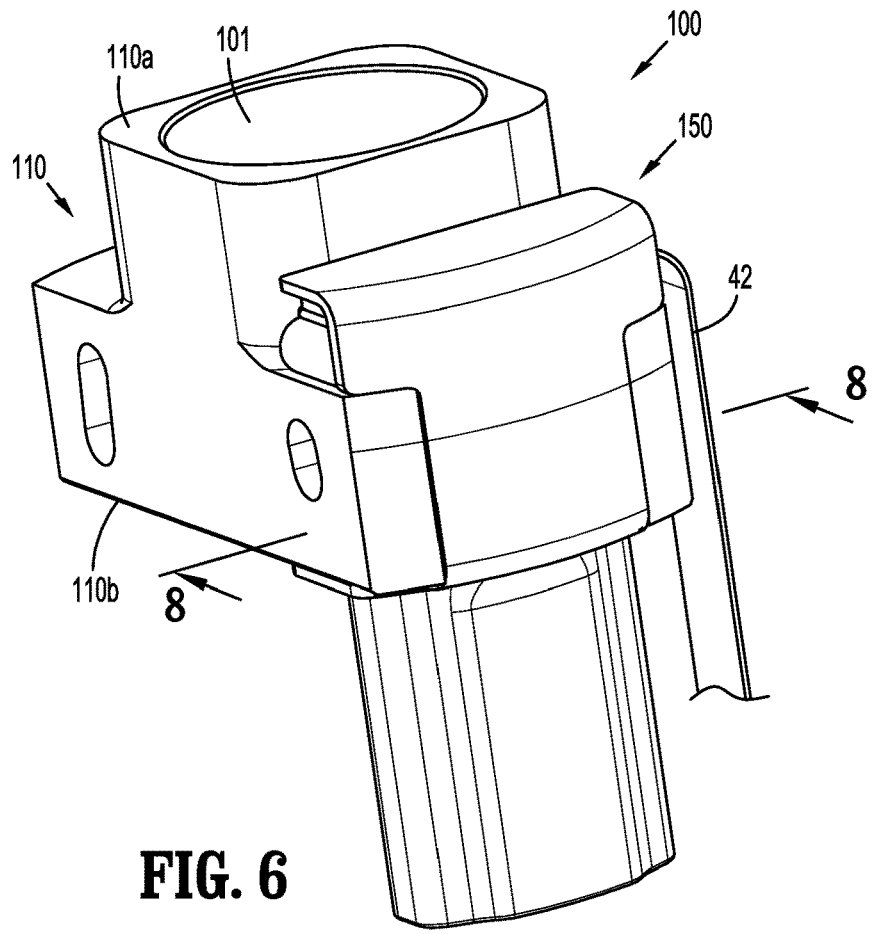

As shown in FIGS. 4-6, the substrate 110 of the force sensor 100 has a central aperture 101 defined through the proximal and distal surfaces 110a, 110b and extending along a central longitudinal axis "X" of the substrate 110. The substrate 110 is divided into first and second lateral halves 111a, 111b by a plane passing through the central longitudinal axis "X". The proximal surface 110a (FIG. 4) and the distal surface 110b (FIG. 5) of the substrate 110 are load bearing surfaces having proximal and distal load contact areas "Cp," "Cd," respectively, as described above, that allow the substrate 110 to compress when loaded by the surgical device 1 (FIG. 1). The substrate 110 is formed from a rigid material having high strength and high temperature endurance, such as a metal (e.g., stainless steel).

As seen in FIG. 4, the proximal surface 110a of the substrate 110 is a stepped surface including a central wall 112a, lateral walls 112b, and intermediate walls 112c interconnecting the central and lateral walls 112a, 112b. The central wall 112a is substantially planar and extends along a plane lying substantially perpendicular to the central longitudinal axis "X" of the substrate 110, and the lateral walls 112b are also planar and extend along a plane lying substantially perpendicular to the central longitudinal axis "X" of the substrate 110 in longitudinally spaced and distal relation relative to the central wall 112a. The intermediate walls 112c are substantially planar and extend along a plane lying substantially parallel to the central longitudinal axis "X" of the substrate 110. It should be understood that the proximal surface 110a may have other configurations, such as, for example, angled lateral walls. As seen in FIG. 5, the distal surface 110b of the substrate 110 is substantially planar and extends along a plane lying substantially perpendicular to the central longitudinal axis "X" (FIG. 4) of the substrate 110 and substantially parallel to the central and lateral walls 112a, 112b (FIG. 4) of the proximal surface 110a.

Figure 7:
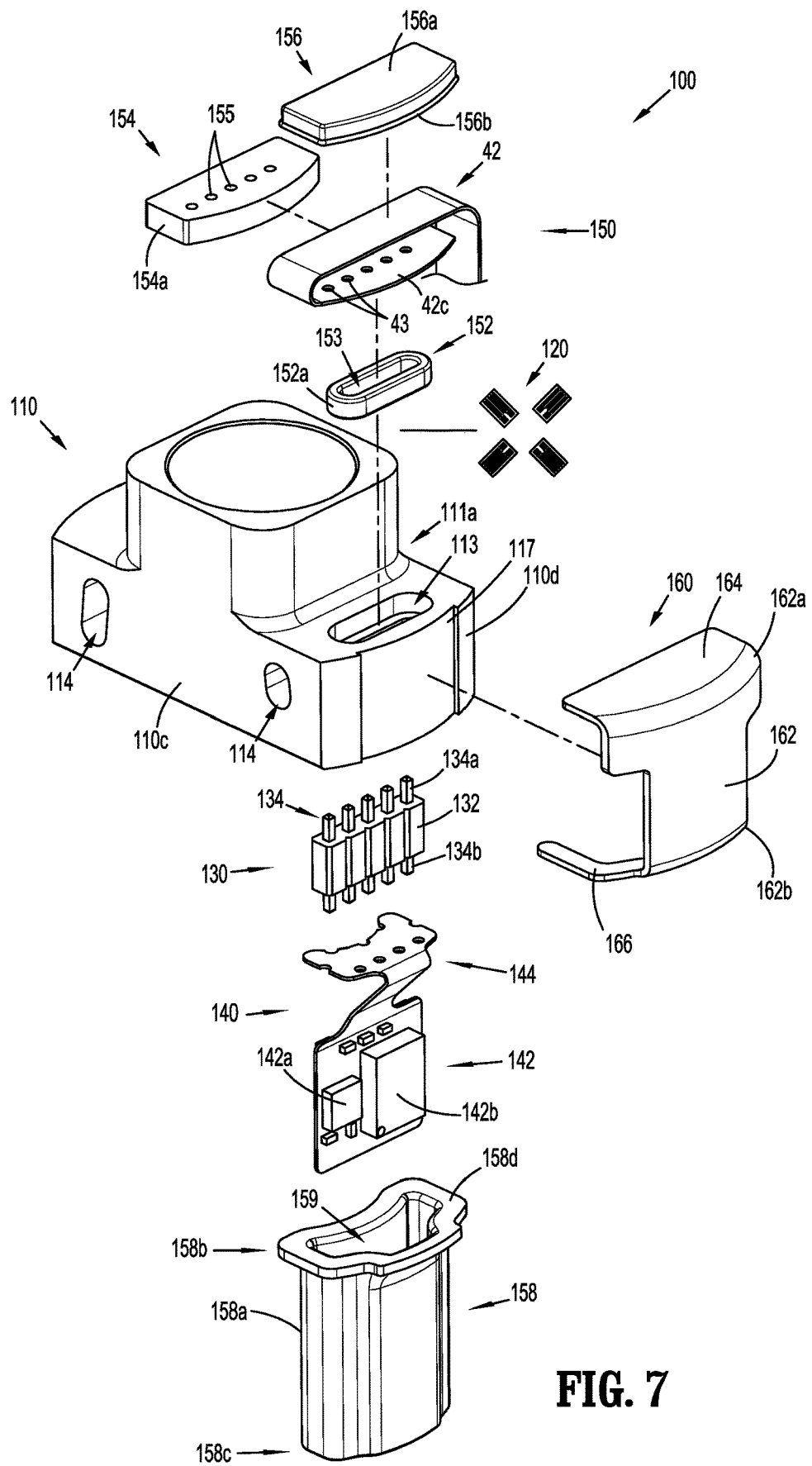
FIG. 7 is a perspective view of the force sensor of FIGS. 4-6, shown with parts separated.
Figure 8:
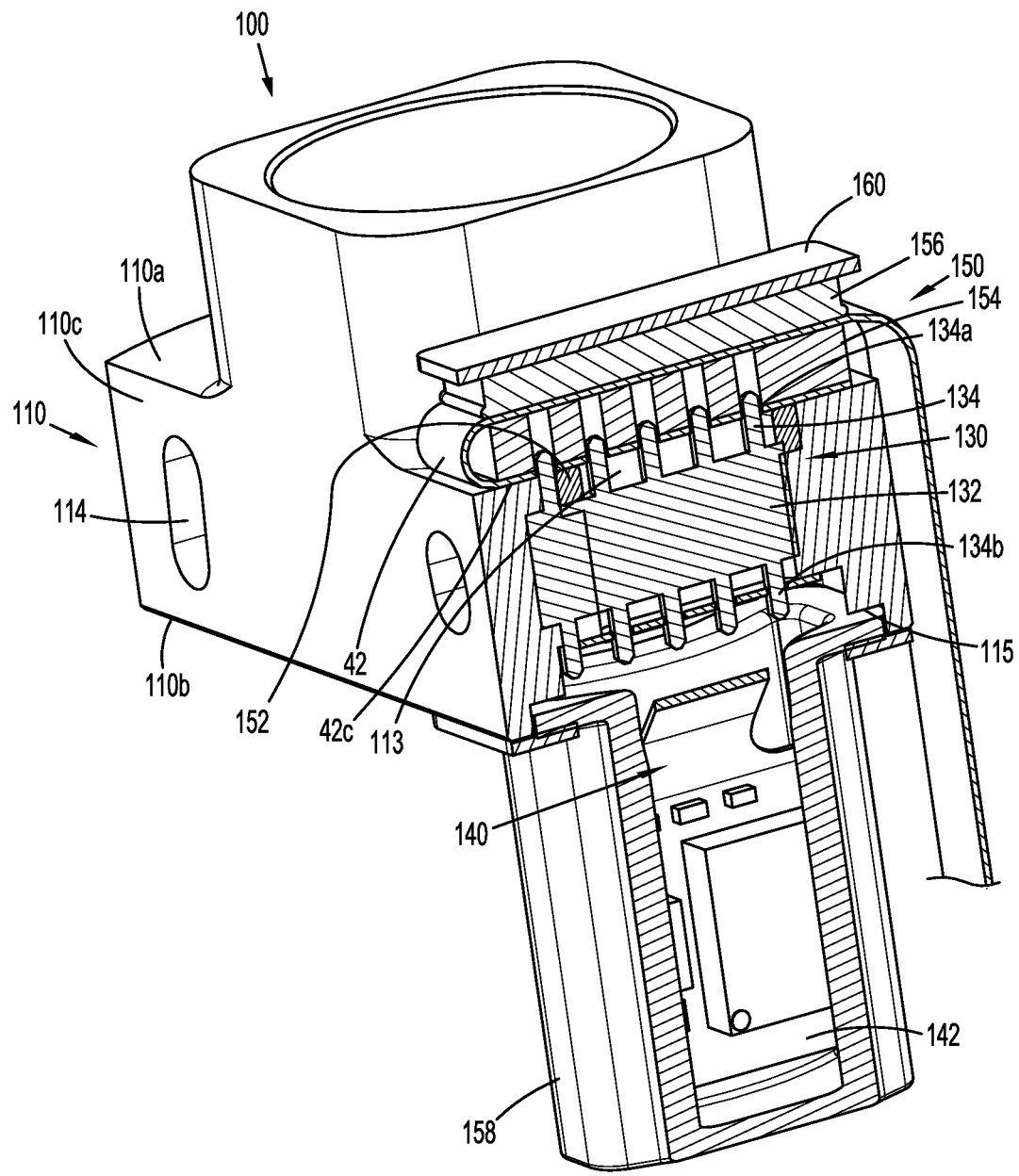
FIG. 8 is a cross-sectional view of the force sensor of FIGS. 4-7, taken along section line 8-8 of FIG. 6.
Figure 10:
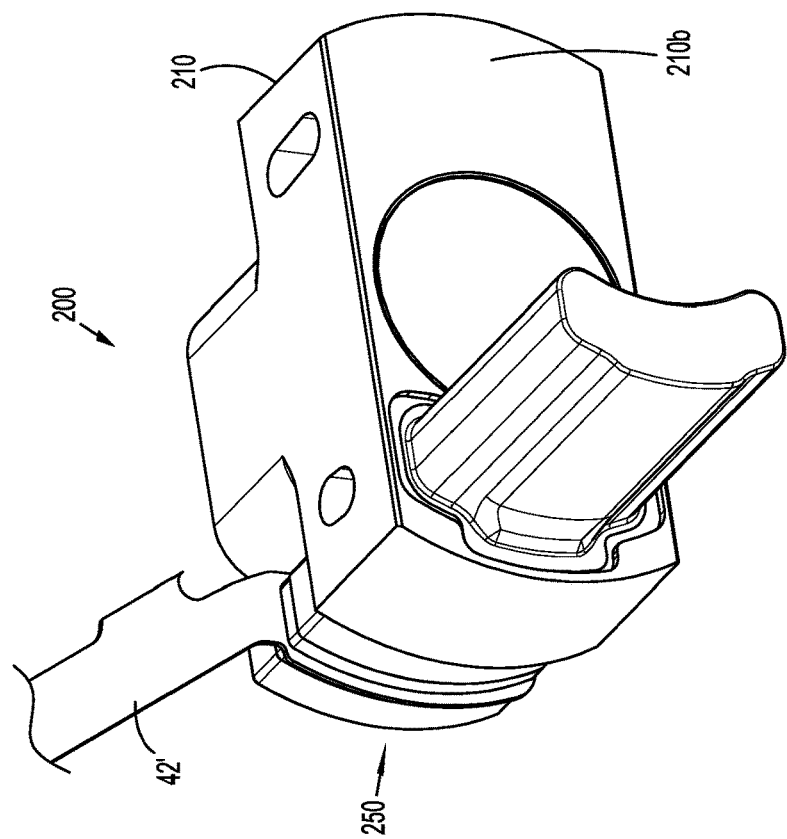
FIGS. 9 and 10 are perspective views of a force sensor in accordance with another aspect of the present disclosure.
Figure 9:
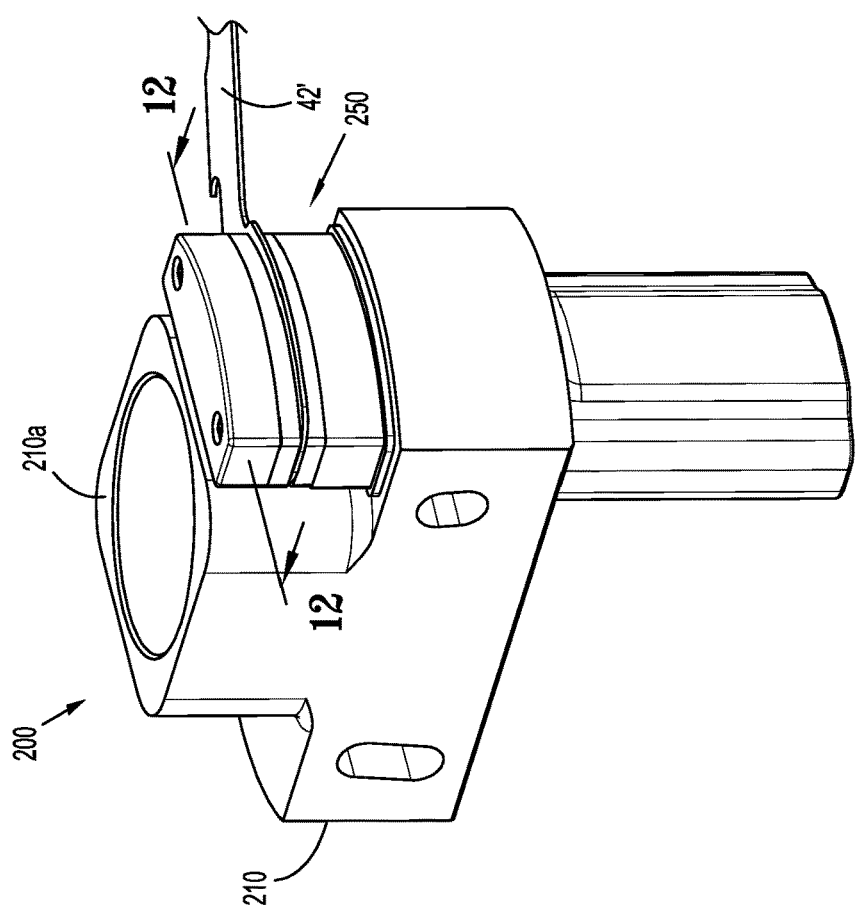
Figure 11:
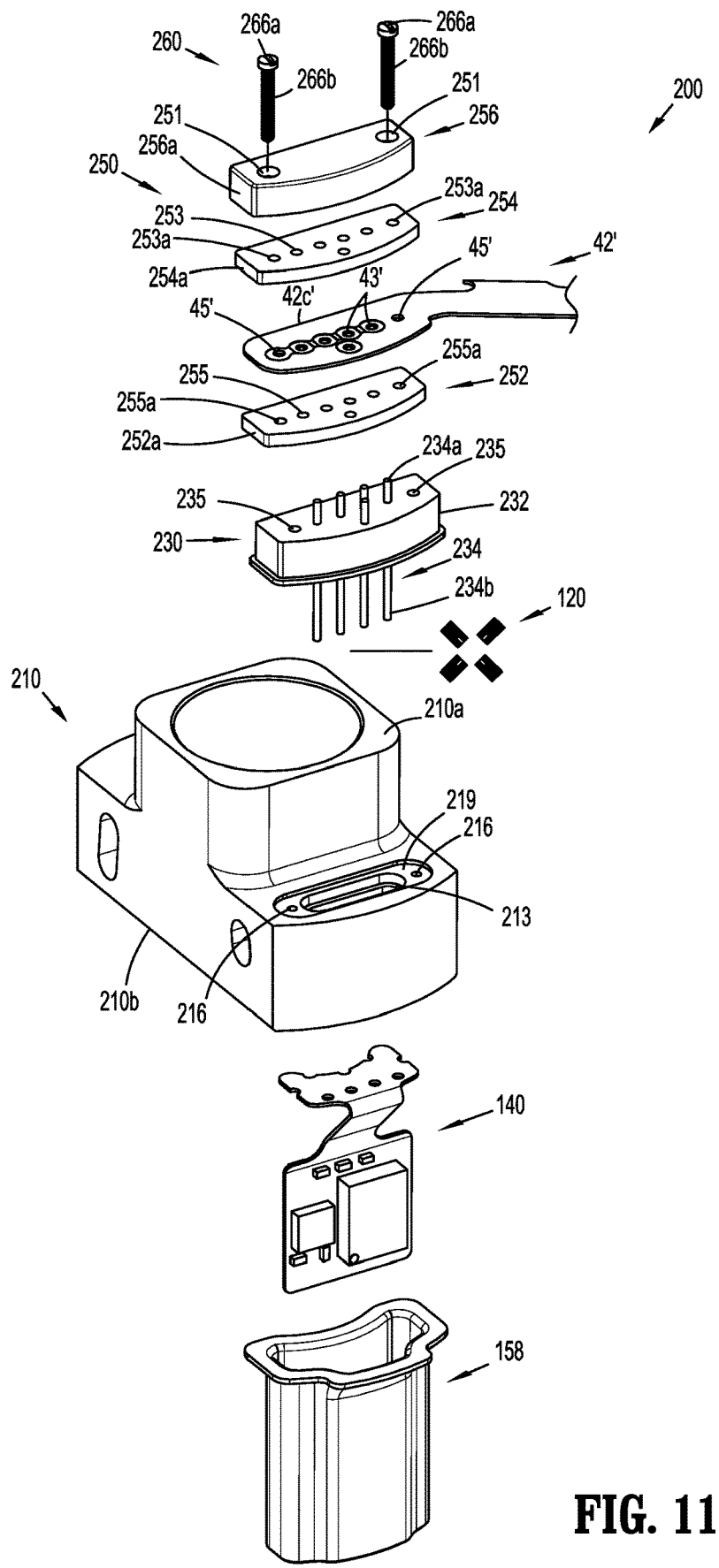
FIG. 11 is a perspective view of the force sensor of FIGS. 9 and 10, shown with parts separated.

Turning now to FIGS. 7 and 8, the force sensor 100 generally includes the substrate 110, sensing elements 120, a pin block assembly 130, an electronics assembly 140, and a seal assembly 150. The substrate 110 includes a cavity 113 defined in the first lateral half 111a that is open at both the proximal and distal surfaces 110a, 110b. The distal surface 110a further includes a groove 115 (FIG. 8) recessed therein that extends around the opening into the cavity 113 for engagement with a cover 158 of the seal assembly 150.

In aspects, the substrate 110 includes relief holes 114 defined in a top surface 110c thereof to facilitate bending and/or to reduce stiffness of the substrate 110. It should be understood that the relief holes 114, as well as other relief features, such as relief cuts, may be formed in the substrate 110 in a variety of shapes and sizes, as well as in different positions about the substrate 110 when more elongation (e.g., flex) is desired.

Figure 12:
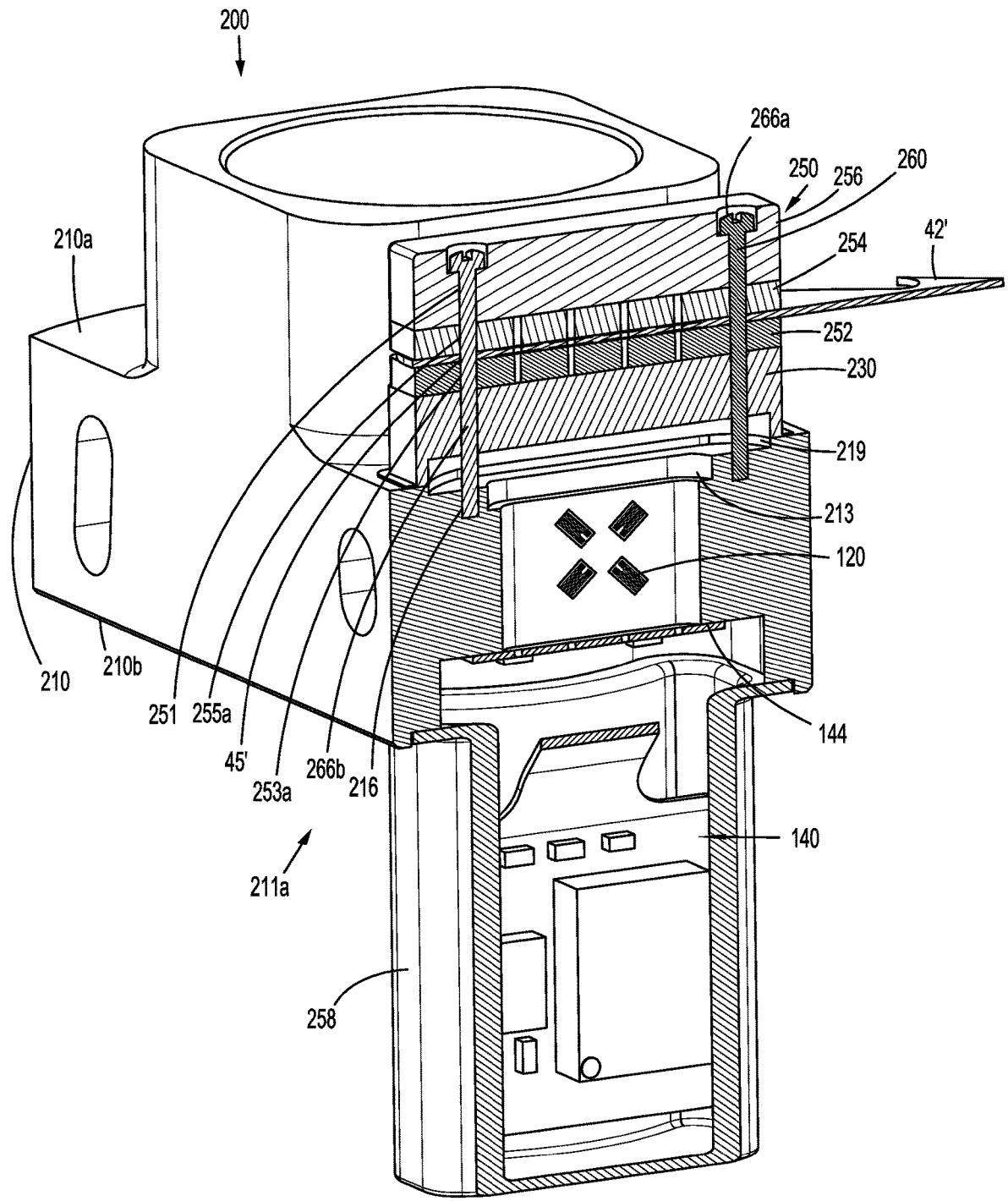
FIG. 12 is a cross-sectional view of the force sensor of FIGS. 9-11, taken along section line 12-12 of FIG. 9.

The sensing elements 120, for example, strain gauges, are disposed within the cavity 113 of the substrate 110 and bonded (e.g., glued) to the substrate 110 (see e.g., FIG. 12) along with associated components thereof (not shown), e.g., media layers, films, protective coatings, circuitry including electronic components, such as resistors, conductive wires and/or traces, and electronic and/or solder connectors, etc. The sensing elements 120 are connected together with a series of wires (not shown) to form a resistance bridge, e.g., a Wheatstone bridge, that can read a linear strain response of the substrate 110 when compressed, as is within the purview of those skilled in the art. Alternatively, the sensing elements 120 may be directly coated or etched onto the substrate 110 by, for example, vapor deposition. In some aspects, the substrate 110 includes a thin insulative layer (e.g., vapor deposited glass) and a thin conductive layer (e.g., nichrome) laser etched to include the sensing elements 120 and the Wheatstone bridge.

The pin block assembly 130 is fixedly secured within the cavity 113 of the substrate 110. The pin block assembly 130 includes a block body 132 and a plurality of pins 134 (referred to herein generally as pins) extending through the block body 132 in spaced relation relative to each other. The block body 132 is formed from an insulative material, such as glass or plastic, and the pins 134 are formed from a conductive material, such as metal. Each of the pins 134 includes a proximal portion 134a and a distal portion 134b extending proximally and distally, respectively, from the block body 132. The sensing elements 120 are electrically coupled to the pins 134, for example, by wires (not shown), within the cavity 113 of the substrate 110. The proximal portions 134a of the pins 134 extend beyond the proximal surface 110a of the substrate 110 for electrical connection with the flex cable 42, and the distal portions 134b of the pins 134 are disposed within the cavity 113 for electrical connection within the electronics assembly 140.

The electronic assembly 140 includes a circuit board 142 and a connector 144 for electrical connection with the distal portions 134b of the pins 134 of the pin block assembly 130. The connector 144 is disposed within the cavity 113 of the substrate 110 and the circuit board 142 extending distally out of the cavity 113 beyond the distal surface 110b of the substrate 110. The circuit board 142 is configured for reading and/or storing data pertaining to the force sensor 100 and sending the data to the powered handle assembly 10 (FIG. 1) via the flex cable 42. The circuit board 142 includes a microprocessor 142a and a memory 142b. The microprocessor 142a is configured to receive and/or measure electrical signals from the sensing elements 120 and record them in the memory 142b which, in turn, is configured to store the data received from the microprocessor 142a. The memory 142b is configured to communicate the data to the handle assembly 10 (FIG. 1) via electrical contact with the pin block assembly 130 and the flex cable 42 which, in turn, is electrically coupled to the handle assembly 10 by the first electrical connector 44 (FIG. 2). The data may be processed by a processor of the power-pack (not shown) of the powered handle assembly 10 (FIG. 1) or in some remote processor or the like. The data may include, for example, stress measurements along the anvil assembly 30 (FIG. 1) which are converted via an algorithm into corresponding tissue stress measurements. It should be understood that the data may correspond with other desired monitored properties of the end effector 20 (FIG. 1) which, in turn, correspond with other desired monitored tissue properties and/or behaviors depending upon the type of sensing elements 120 and/or sensor utilized in the anvil assembly 30.

The seal assembly 150 secures the flex cable 42 to the substrate 110 and seals the cavity 113 of the substrate 110 to protect the sensing elements 120, the pin block assembly 130, and the electronics assembly 140 disposed therein. The seal assembly 150 includes first and second gaskets 152, 154, a retainer plate 156, a cover 158, and a seal restraint 160. The first or header gasket 152 is sized and shaped for positioning within the cavity 113 between the block body 132 of the pin block assembly 130 and the proximal surface 110a of the substrate 110. The first gasket 152 includes a gasket body 152a defining an opening 153 therethrough. The gasket body 152a is configured to abut the block body 132 and to be flush with the proximal surface 110a of the substrate 110 such that the proximal portions 134a of the pins 134 of the pin block assembly 130 extend through the opening 153 defined in the gasket body 152a and proximally beyond the proximal surface 110a of the substrate 110. The opening 153 of the first gasket 152 may be a single, continuous opening or include a plurality of openings aligned or in registration with the pins 134. The first gasket 152 is formed from a high temperature compliant material, such as an elastomeric material (e.g., silicone, rubber, or combinations thereof, such as those sold under the trademark Elastosil® of Wacker Chemie AG) to aid in sealing the opening into the cavity 113 of the substrate 110.

The third portion 42c of the flex cable 42 is sized and shaped for positioning over the cavity 113 on the proximal surface 110a of the substrate 110 and is dimensioned to be larger in size than the opening into the cavity 113 such that the flex cable 42 lays substantially flush against the proximal surface 110a of the substrate 110 and the first gasket 152 is disposed within the cavity 113. The third portion 42c of the flex cable 42 includes a plurality of apertures 43 defined therethrough that are sized, shaped, and positioned to receive the pins 134 of the pin block assembly 130 therethrough. The third portion 42c of the flex cable 42 is positioned over the first gasket 152 of the seal assembly 150 such that the proximal portions 134a of the pins 134 of the pin block assembly 130 engage and extend through the plurality of apertures 43 of the flex cable 42.

The second gasket 154 is sized and shaped for positioning over the third portion 42c of the flex cable 42. The second gasket 154 includes a gasket body 154a defining a plurality of openings 155 therethrough that are aligned or in registration with the pins 134 of the pin block assembly 130. The second gasket 154 is positioned over the third portion 42c of the flex cable 42 such that the proximal portions 134a of the pins 130 extend into and are disposed within the plurality of openings 155 of the second gasket 154, as seen in FIG. 8. The second gasket 154 is formed from a high temperature compliant material, such as an elastomeric material (e.g., the same as or similar to the first gasket 152), that is compressible against the pins 130 and the flex cable 42 to aid in sealing the opening into the cavity 113 of the substrate 110. In some aspects, the second gasket 154 is formed from a more flexible material than the first gasket 152. In aspects in which the third portion 42c of the flex cable is defined in an end of the flex cable 42, the flex cable 42 is wrapped around the second gasket 154, as seen, for example, in FIG. 8, such that the second gasket 154 is sandwiched between the flex cable 42.

The retainer plate 156 is sized and shaped for positioning against the flex cable 42. The retainer plate 156 includes a flat body 156a having a lip 156b extending around a distal end of the flat body 156a. The retainer plate 156 is positioned against the flex cable 42 to mechanically compress the second gasket 154 towards the proximal surface 110a of the substrate 110. The retainer plate 156 is formed from a rigid material that is non-toxic, chemically inert, and capable of withstanding high temperatures and harsh detergents, such as, for example, a metal (e.g., stainless steel) or a polymer (e.g., polyphenylsulfone, such as those sold under the trademark Radel® by Solvay Specialty Polymers USA, L.L.C.).

Alternatively, the retainer plate 156 may define a cavity (not shown) therein that is configured to receive the flex cable 42 and the second gasket 154 therein. In such aspects, the lip 156b of the retainer plate 156 abuts the proximal surface 110a of the substrate 110 as well as the portion of the flex cable 42 extending outwardly therefrom, thereby compressing the second gasket 154 within the retainer plate 156.

The cover 158 is sized and shaped to house the circuit board 142 of the electronics assembly 140 therein. The cover 158 includes an elongated body 158a having an open proximal end 158b and a closed distal end 158c thereby defining a pocket 159 therein. A flange 158d extends around an entire outer perimeter of the open proximal end 158b for engagement with the distal surface 110b of the substrate 110 and, more specifically, for positioning within the groove 115 defined in the distal surface 110b. In some aspects, at least the flange 158d of the cover 158 and, in certain aspects, the entire cover 158 is formed from a polymeric material, such as an elastomer having a low durometer, to effectively seal the distal surface 110b of the substrate 110 over which the cover 158 is disposed in a fluid tight manner by a relatively low closure force provided by the seal restraint 160 of the seal assembly 150. In aspects, the cover 158 is fabricated from a rigid material (e.g., the same as or similar to the retainer plate 156).

Alternatively, in some aspects, the electronics assembly 140 may be integrated into the flex cable 42 and the cavity 113 of the substrate 110 is only open to the proximal surface 110a of the substrate 110. In such aspects, the force sensor 100 does not include the electronics assembly 140 or the cover 158 of the seal assembly 150.

The seal restraint 160 is in the form of a compression clip, and is sized and shaped for positioning around the first lateral half 111a of the substrate 110 to secure the seal assembly 150 to the substrate 110. The compression clip 160 includes a side wall 162 configured to extend along a side surface 110d of the substrate 110. In aspects, the side wall 162 of the compression clip 160 is positioned within a recess 117 defined in the side surface 110d of the substrate 110 such that the compression clip 160 is flush with the side surface 110d. The compression clip 160 further includes a proximal wall 164 extending transversely from the side wall 162 at a first or proximal end 162a thereof for engaging (e.g., covering) the retainer plate 156 and securing the first and second gaskets 152, 154 as well as the third portion 42c of the flex cable 42 to the proximal surface 110 of the substrate 110, and a distal wall 164 extending transversely from the side wall 162 at a second or distal end 162b thereof for engaging and securing the cover 158, and more specifically, the flange 158d, to the distal surface 110b of the substrate 110. While the distal wall 164 is shown as being bifurcated, the distal wall 164 may be a continuous wall defining an opening therethrough that is configured to receive the cover 158 therethrough and press the flange 158d against the distal surface 110b of the substrate 110.

The compression clip 160 mechanically compresses the seal assembly 150 against the substrate 110 to hermetically seal the sensing elements 120, the pin block assembly 130, and the electronics assembly 140 within the cavity 113 of the substrate 110. The compression clip 160 applies a constant pressure onto the components of the seal assembly 150 to prevent the ingress of fluids (e.g., liquids) during a cleaning or sterilization cycle thereby protecting the electronic components from the external environment. Specifically, the compression clip 160 applies pressure onto the retainer plate 156 towards the proximal surface 110a of the substrate 110 which, in turn, applies pressure onto the second gasket 154 and the flex cable 42 such that the second gasket 154 and flex cable 42 is compressed against the proximal surface 110a of the substrate 110 to close the opening into the cavity 113 on the proximal side of the substrate 110. The compression clip 160 also applies pressure and compresses the flange 158d of the cover 158 towards and against the distal surface 110b of the substrate 110 to close the opening into the cavity 113 on the distal side of the substrate 110. Accordingly, the compression clip 160 is held in place by the spring force from the compressed first and second gaskets 152, 154 and flange 158d. In some aspects, the cover 158 of the seal assembly 150 may be additionally secured to the substrate 110 by conventional methods, such as the use of adhesives or coatings, among other techniques within the purview of those skilled in the art. The compression clip is fabricated from a rigid material, such as metal or plastic.

Turning now to FIGS. 9-12, a force sensor 200 in accordance with another aspect of the present disclosure is shown for use in the surgical device 1 (FIG. 1). The force sensor 200 generally includes a substrate 210, sensing elements 120, a pin block assembly 230, an electronics assembly 140, and a seal assembly 250. The force sensor 200 is electrically coupled to a flex cable 42', as described above with regard to force sensor 100. The force sensor 200 and the flex cable 42' are substantially similar to the force sensor 100 and the flex cable 42 of FIGS. 2-8 and will be described with respect to the differences therebetween. Accordingly, it should be understood that various components of the disclosure, such as those numbered in the 100 series or plainly numbered, correspond to components of the disclosure similarly numbered in the 200 series or prime numbered, such that redundant explanation of similar components need not be repeated herein.

The substrate 210 is substantially the same as the substrate 110 (FIG. 4) of the force sensor 100, except that the proximal surface 210a further includes a groove 219 recessed therein that extends around the opening into the cavity 213 for engagement with the pin block assembly 230. Holes 216 are defined through the proximal surface 210a and on opposed sides of the cavity 213 within the groove 219. In aspects, the holes 216 are threaded for engagement with a seal restraint 260 of the seal assembly 250.

The pin block assembly 230 includes a block body 232 and a plurality of pins 234 extending through the block body 232. The block body 232 further includes through holes 235 extending therethrough on opposed sides of the pins 234 that are aligned or in registration with the holes 216 of the substrate 210.

The seal assembly 250 includes first and second gaskets 252, 254, a retainer plate 256, a cover 158, and a seal restraint 260. Each of the first and second gaskets 252, 254 includes a gasket body 252a, 254a defining a plurality of openings 253, 255 therethrough that are aligned or in registration with the pins 234 of the pin block assembly 230, and further includes through holes 253a, 255a that are aligned or in registration with the through holes 235 of the pin block assembly 230. The first and second gaskets 252, 254 are formed from a flexible material, such as an elastomeric material (e.g., silicone rubber) that have sealing and adhesive properties and durability. The retainer plate 256 includes a flat body 256a defining through holes 251 therethrough aligned or in registration with the through holes 235 of the pin block assembly 230.

The flex cable 42' is substantially the same as flex cable 42 (FIG. 6), except that the third portion 42c' of the flex cable 42', in addition to including the plurality of apertures 43' that are sized, shaped, and positioned to receive the pins 234 of the pin block assembly 230 therethrough, includes through holes 45' that are sized, shaped, and positioned to receive the seal restraint 260 therethrough.

The seal restraint 260 is in the form of screws, with each screw 260 including a head 266a and a threaded shank 266b extending from the head 266a. The screws 260 are sized and shaped for positioning through the through holes 253a, 255a of the first and second gaskets 252, 254, the through holes 235 of the pin block assembly 230, the through holes 45' of the flex cable 42', and into the holes 216 of the substrate 210.

Figure 13:
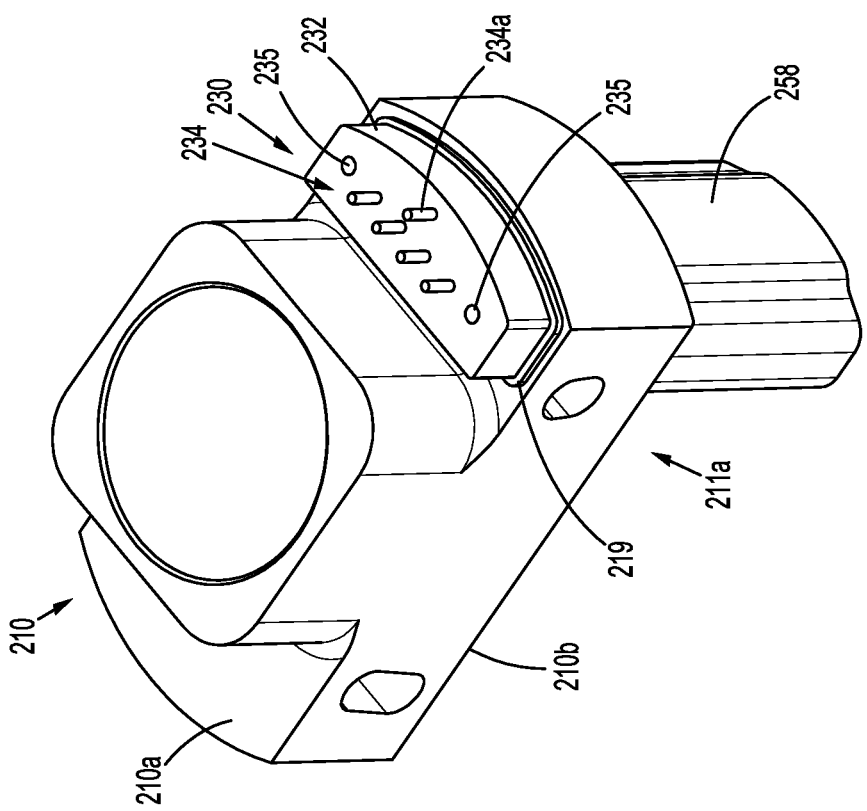

A method of assembling the seal assembly 250 onto the force sensor 200 is shown in FIGS. 13-18. With the sensing elements 120 (FIG. 12) positioned and secured to the substrate 210 within the cavity 213, the pin block assembly 230 is positioned on the first lateral half 211a of the proximal surface 210a of the substrate 210 such that distal portions 234b (FIG. 11) of the pin 234 are disposed within the cavity 213 of the substrate 210 and the block body 232 is positioned adjacent to the proximal surface 210a of the substrate 210 and seated within the groove 219, as seen in FIG. 13. The sensing elements 120 (FIG. 12) are electrically coupled to the distal portions 234b (FIG. 11) of the pins 234 via, e.g., wires (not shown), as described above and the connector 144 (FIG. 12) of the electronics assembly 140 is positioned within the cavity 213 of the substrate 210 and coupled to the distal portions 234b of the plurality of pins 234 via, e.g., wires (not shown) for electrical connection with the circuit board 142, which extends distally out of the substrate 210. The cover 258 is positioned over the electronics assembly 140 (FIG. 12) and secured to the distal surface 210b of the substrate 210, e.g., by welding, adhesives, coatings, and/or mechanical connections (e.g., the same as or similar to the seal restraint 160, 260) to seal the cavity 213 on the distal side of the substrate 210.

Figure 14:
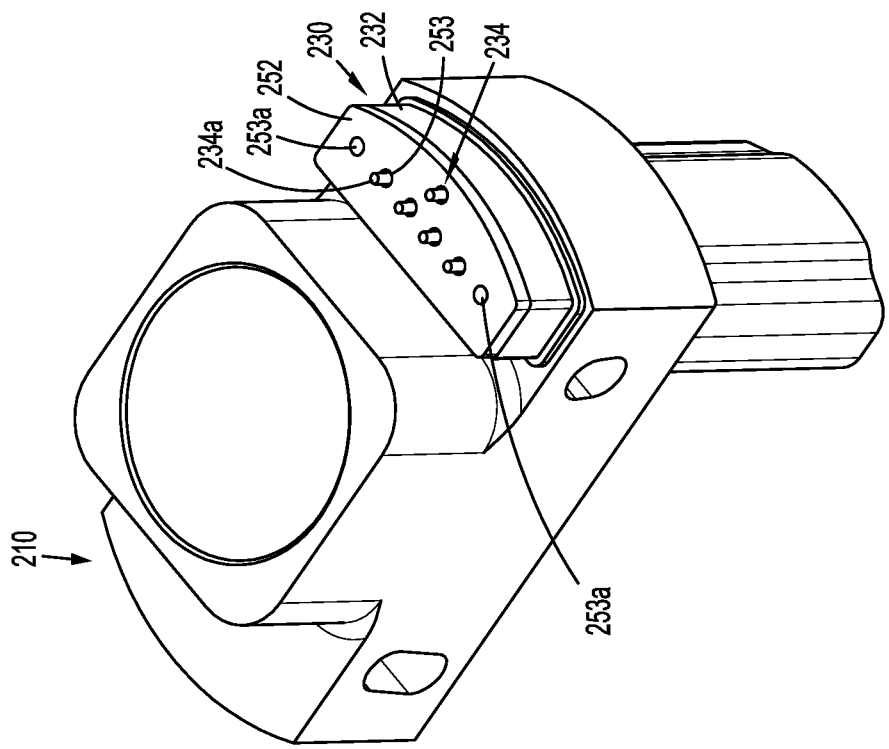
FIGS. 13-18 are perspective views of the force sensor of FIGS. 9-12, illustrating the assembly of a seal assembly of the force sensor to a substrate of the force sensor in accordance with an aspect of the present disclosure.

As shown in FIG. 14, the first gasket 252 is then placed atop the block body 232 of the pin block assembly 230 with the proximal portions 234a of the pins 234 extending through the openings 253 of the first gasket 252 and the through holes 253a aligned with the through holes 235 (FIG. 13) of the block body 232 such that the first gasket 252 lays flush against the block body 232.

Figure 15:
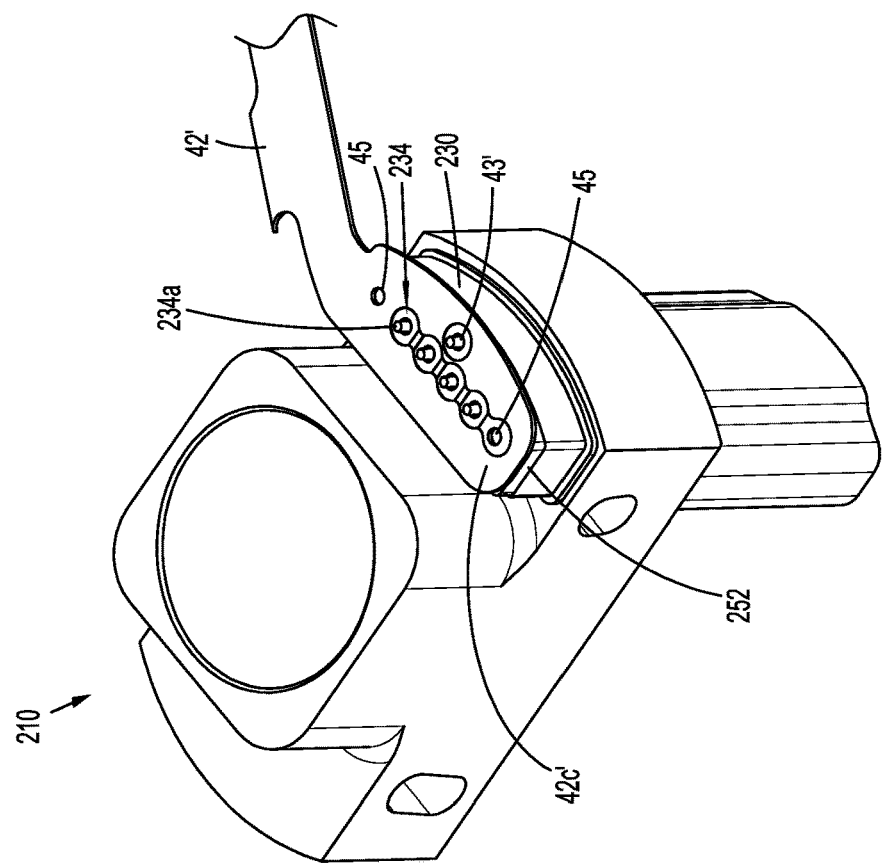

As seen in FIG. 15, the third portion 42c' of the flex cable 42' is then positioned over the first gasket 252 such that the proximal portions 234a of the pins 234 of the pin block assembly 230 extend through the plurality of apertures 43' of the flex cable 42' and the through holes 45 are aligned with the through holes 253a (FIG. 14) of the first gasket 252 such that the third portion 42c' of the flex cable 42' lays flush against the first gasket 252.

Figure 16:
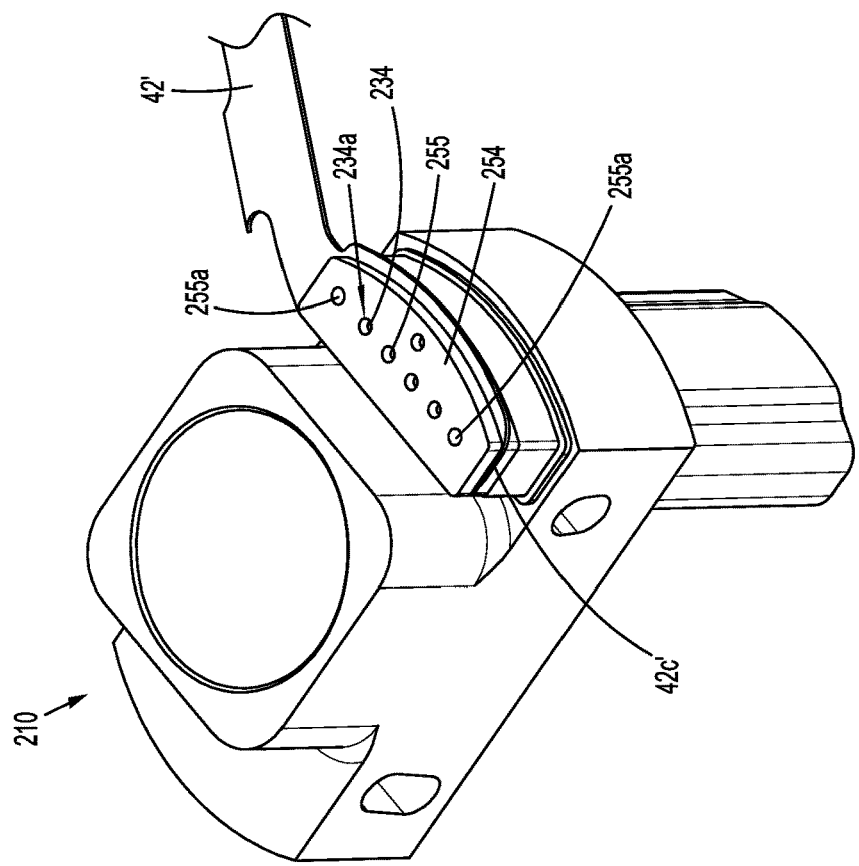

As seen in FIG. 16, the second gasket 254 is positioned over the third portion 42c' of the flex cable 42' such that the proximal portions 234a of the pins 234 extend into and are disposed within the plurality of openings 255 of the second gasket 254 and the through holes 255a are aligned with the through holes 45 (FIG. 15) of the flex cable 42'. The second gasket 254 lays flush against the flex cable 42'.

Figure 18:
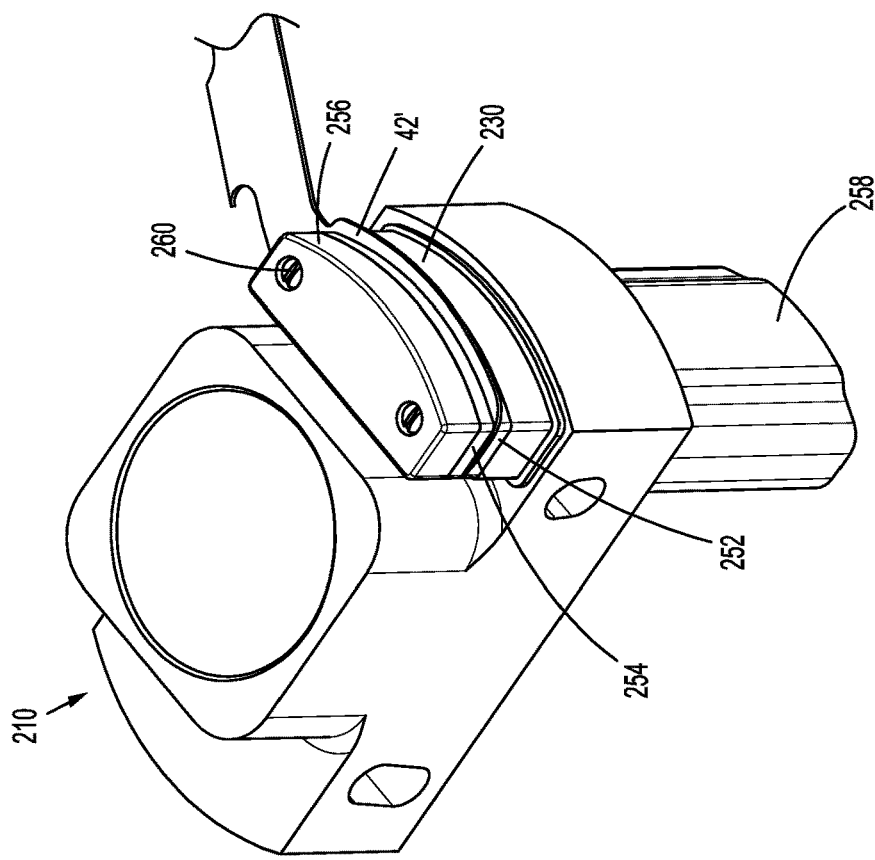
Figure 17:
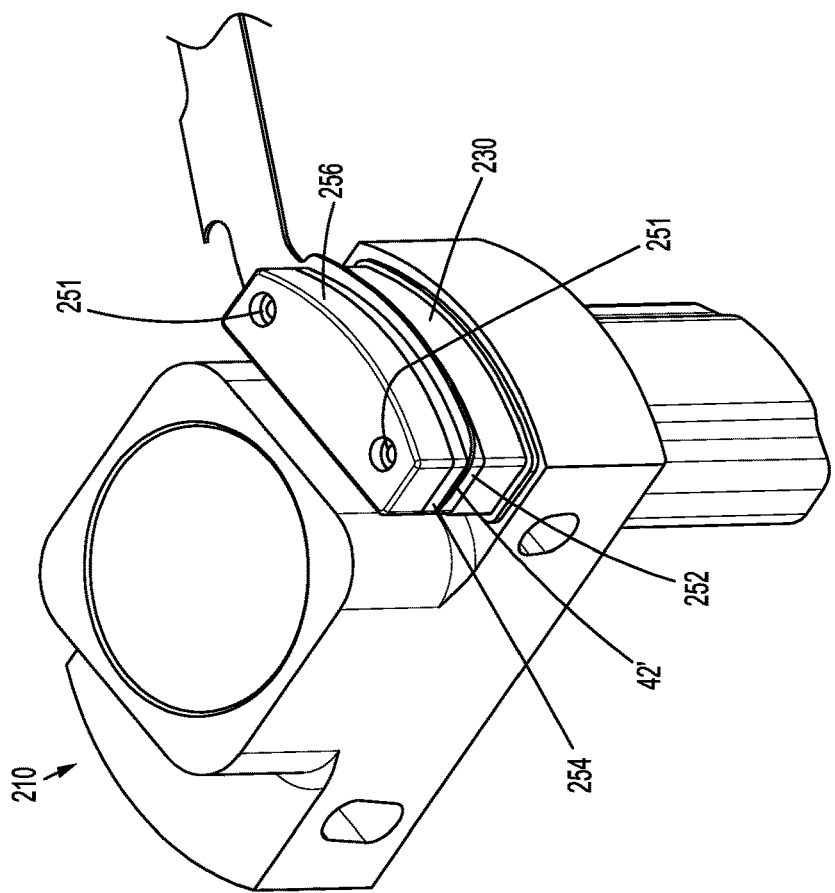

As seen in FIG. 17, the retainer plate 256 is positioned over the second gasket 254 with the through holes 251 aligned with the through holes 255a (FIG. 16) of the second gasket 254. As seen in FIG. 18, in conjunction with FIG. 12, the threaded shanks 266b of the screws 260 are then inserted through the through holes 251 of the retainer plate 256, the through holes 255a of the second gasket 254, the through holes 45' of the flex cable 42', the through holes 253a of the first gasket 252, and into the holes 216 of the substrate 210, and the heads 266a of the screws 260 are seated within the retainer plate 256.

The screws 260 secure the pin block assembly 230, the first and second gaskets 252, 254, the flex cable 42', and the retainer plate 256 to the substrate 210 and applies pressure onto the retainer plate 256 to compress the first and second gaskets 252, 254 between the retainer plate 256 and the block body 232 of the pin block assembly 230. The screws 260 apply constant pressure on the components of the seal assembly 250 to effective seal the electronic components therein.

While the force sensors 100, 200 are shown including sensing elements and a seal assembly associated with the first lateral half of the substrate, it should be understood that additionally or alternatively, the force sensors 100, 200 may include a cavity in the second lateral half of the substrate. At least because the first and second lateral halves of the substrate are mirror images of each other, a person of ordinary skill in the art will readily understand that the seal assemblies are configured to accommodate such alternate or additional configurations. In aspects in which the sensing elements are disposed in each of the first and second lateral halves of the substrate, two seal assemblies would be utilized with the force sensor, as can be readily appreciated by one skilled in the art.

It should be understood that the seal assembly may vary. For example, additional gaskets may be provided and/or alternate seal restraints may be utilized used to hold the seal assembly under compressive load. Accordingly, while the seal restraints are shown as a compression clip and as screws, other configurations are envisioned (e.g., straps).

The surgical device is used, for example, in an anastomosis procedure to effect joining of two tubular or hollow tissue sections (e.g., intestinal section) together. Generally, referring again to FIG. 1, the anvil assembly 24 may be applied to the operative site either through a surgical incision or natural orifice (e.g., transanally) and positioned within a first tissue or intestinal section (not shown) and secured temporarily thereto (e.g., by a purse string suture), and the loading unit 22 and the outer sleeve 32 (FIG. 2) of the adapter assembly 30 may be inserted into a second tissue or intestinal section (not shown) and secured temporarily thereto. Thereafter, a clinician maneuvers the anvil assembly 24 until the proximal end of the anvil rod 24b is inserted into the distal end of the adapter assembly 30, wherein mounting structure (not shown) within the distal end of the adapter assembly 30 engages the anvil rod 24b to effect mounting. The anvil assembly 24 and the loading unit 22 are then approximated to approximate the first and second tissue sections. The surgical device 1 is then fired, and a knife (not shown) cuts the portion of tissue disposed radially inward of the knife, to complete the anastomosis.

The force sensors 100, 200 of the present disclosure may be utilized to enhance the anastomosis procedure by controlling a function of the surgical device 1. For example, the force sensors may be used to control the force and/or rate of compression of tissue. If tissue is compressed too rapidly, it may become bruised, torn, damaged, etc. during such compression. Without being bound to any particular theory, it is believed that maintaining a constant force of compression on the tissue provides a steady yet rapid compression of tissue until the optimal staple gap is achieved for performing stapling and cutting functions. The force sensors may be utilized to first read the force to compress the tissue. Once compressed, the force sensors may also monitor the stapling function. Such monitoring allows for the programming of the stapling function. In aspects, the surgical device is programmed to deliver a preset load depending on the anvil selected. For example, a smaller anvil requires a lower force than a larger anvil. In aspects, the cutting function may be controlled to stop at a predetermined force. This allows for the electronics and software to control such functions eliminating the need for tight mechanical stops.

While illustrated as being used in a hand-held powered surgical device 1 hereinabove, it is contemplated, and within the scope of the present disclosure for the force sensor 100, 200 to be configured for use with various electromechanical and/or electrosurgical instruments and systems. For example, the force sensors may be utilized in non-motor driven yet powered surgical devices (e.g., reusable surgical devices subject to washing and/or sterilization procedures). As another example, the force sensors may be utilized in robotic surgical systems, such as the robotic surgical system shown and described in U.S. Patent Appl. Pub. No. 2012/0116416, now U.S. Pat. No. 8,828,023, the entire content of which is incorporated herein by reference.

While aspects of the disclosure have been shown in the drawings, it is not intended that the disclosure be limited thereto, as it is intended that the disclosure be as broad in scope as the art will allow and that the specification be read likewise. It is to be understood, therefore, that the disclosure is not limited to the precise aspects described, and that various other changes and modifications may be effected by one skilled in the art without departing from the scope or spirit of the disclosure. Additionally, the elements and features shown and described in connection with certain aspects of the disclosure may be combined with the elements and features of certain other aspects without departing from the scope of the present disclosure, and that such modifications and variation are also included within the scope of the present disclosure. Therefore, the above description should not be construed as limiting, but merely as exemplifications of aspects of the disclosure and the subject matter of the present disclosure is not limited by what has been particularly shown and described. Thus, the scope of the disclosure should be determined by the appended claims and their legal equivalents, rather than by the examples given.

What is claimed is:

1. A force sensor comprising:
a substrate having a proximal surface and a distal surface, the substrate defining a cavity therein open to the proximal surface;
sensing elements disposed within the cavity of the substrate;
a pin block assembly mounted within the cavity of the substrate and electrically coupled to the sensing elements;
a first gasket disposed within the cavity of the substrate over the pin block assembly;
a flex cable positioned against the proximal surface of the substrate over the cavity, the flex cable electrically coupled to the pin block assembly;
a second gasket positioned over the flex cable;
a retainer plate positioned over the second gasket; and
a seal restraint coupled to the substrate and extending over the retainer plate, the seal restraint applying pressure on the retainer plate and compressing the second gasket against the flex cable to seal the cavity of the substrate.

2. The force sensor according to claim 1, wherein the sensing elements are strain gauges.

3. The force sensor according to claim 1, wherein the pin block assembly including a block body and pins extending through the block body, each of the pins having a proximal portion and a distal portion extending proximally and distally, respectively, from the block body, the proximal portions of the pins extending proximally out of the cavity of the substrate and the distal portions of the pins disposed within the cavity.

4. The force sensor according to claim 3, wherein the first gasket defines at least one opening therethrough, and the proximal portions of the pins of the pin block assembly extend proximally through the at least one opening of the first gasket.

5. The force sensor according to claim 3, wherein the flex cable includes a plurality of apertures defined therethrough, and the proximal portions of the pins of the pin block assembly extend proximally through the plurality of apertures.

6. The force sensor according to claim 3, wherein the second gasket defines openings therethrough, and the proximal portions of the pins of the pin block assembly are disposed within the openings of the second gasket.

7. The force sensor according to claim 1, wherein the flex cable is wrapped over a proximal end of the second gasket, and the retainer plate is positioned against the flex cable.

8. The force sensor according to claim 1, wherein the cavity of the substrate is open to the distal surface, and the force sensor further includes an electronics assembly electrically coupled to the pin block assembly and extending distally out of the cavity.

9. The force sensor according to claim 8, further including a cover disposed over the electronics assembly and positioned against the distal surface of the substrate over the cavity, the seal restraint extending over and compressing the cover against the distal surface to seal the cavity on the distal surface of the substrate.

10. The force sensor according to claim 9, wherein the seal restraint is a compression clip including a proximal wall engaged with the retainer plate and a distal wall engaged with the cover.

11. A surgical device comprising:
a powered handle assembly;
an adapter assembly including a distal connector housing and a trocar connection housing;

an end effector releasably secured to the distal connector housing of the adapter assembly; and the force sensor of claim 1 disposed between the distal connector housing and the trocar connection housing, and configured to measure forces exhibited by the end effector along a load path.

12. The surgical device according to claim 11, wherein the flex cable is electrically coupled to the powered handle assembly and the end effector assembly such that the forces measured by the force sensor is communicated to the powered handle assembly to effect a function of the end effector.

13. A force sensor comprising:

a substrate having a proximal surface and a distal surface, the substrate defining a cavity therein open to the proximal surface;

sensing elements disposed within the cavity of the substrate;

a pin block assembly mounted on the proximal surface of the substrate over the cavity, the pin block assembly electrically coupled to the sensing elements;

a first gasket positioned over the pin block assembly;

a flex cable positioned over the first gasket and electrically coupled to the pin block assembly;

a second gasket positioned over the flex cable;

a retainer plate positioned over the second gasket; and a seal restraint coupled to the substrate, the seal restraint applying pressure on the retainer plate and compressing the second gasket, the flex cable, the first gasket, and the pin block assembly against the proximal surface of the substrate to seal the cavity of the substrate.

14. The force sensor according to claim 13, wherein the sensing elements are strain gauges.

15. The force sensor according to claim 13, wherein the pin block assembly including a block body and pins extending through the block body, each of the pins having a proximal portion and a distal portion extending proximally and distally, respectively, from the block body, the distal portions of the pins disposed within the cavity.

16. The force sensor according to claim 13, wherein the proximal surface of the substrate includes holes defined therein, and the seal restraint extends into the holes.

17. The force sensor according to claim 16, wherein each of the first gasket, the flex cable, the second gasket, and the retainer plate define through holes therethrough that are aligned with the holes defined in the substrate.

18. The force sensor according to claim 17, wherein the seal restraint incudes screws extending through the through holes of the retainer plate, the second gasket, the flex cable, and the first gasket, and into the holes of the substrate.

19. The force sensor according to claim 13, wherein the cavity of the substrate is open to the distal surface, and the force sensor further includes an electronics assembly electrically coupled to the pin block assembly and extending distally out of the cavity.

20. The force sensor according to claim 19, further including a cover disposed over the electronics assembly and positioned against the distal surface of the substrate to seal the cavity on the distal surface of the substrate.

* * * * *